United States Patent [19]
Shaw

[11] Patent Number: 5,419,179
[45] Date of Patent: May 30, 1995

[54] HYGROMETERS

[76] Inventor: J. Leonard Shaw, Les Roches Fleuries, Fort George, Guernsey, Channel Islands

[21] Appl. No.: 141,097

[22] Filed: Oct. 26, 1993

[30] Foreign Application Priority Data

Oct. 27, 1992 [GB] United Kingdom ............... 9222565

[51] Int. Cl.$^6$ ..................... G01N 19/10; G01W 1/18
[52] U.S. Cl. ........................... 73/29.02; 73/76
[58] Field of Search ................... 73/29.02, 76

[56] References Cited

U.S. PATENT DOCUMENTS

| 3,110,173 | 11/1963 | Bishop | 73/29.02 |
| 3,832,882 | 9/1974 | Schoen, Jr. | 73/29.02 |
| 3,937,063 | 2/1976 | Kethley | 73/29.02 |
| 4,419,888 | 12/1983 | Kitamura et al. | 73/29.02 |

FOREIGN PATENT DOCUMENTS 9202802  2/1992  Sweden ........................... 73/29.02

Primary Examiner—Hezron E. Williams
Assistant Examiner—J. David Wiggins
Attorney, Agent, or Firm—Nikaido Marmelstein Murray & Oram

[57] ABSTRACT

According to the invention a hygrometer is provided for measuring the moisture content of a gas, the hygrometer comprising a chamber 2 housing a hygrometer sensor 1, a gas inlet 3 for admitting gas into the chamber and a gas outlet 4 for allowing gas to leave the chamber, the apparatus being such that a drying medium can be stored in the chamber to dry the sensor and then be rapidly removed from the chamber prior to measurement, for example via a removable lid 5.

9 Claims, 1 Drawing Sheet

HYGROMETERS

BACKGROUND TO THE INVENTION

The invention relates to hygrometers.

To operate effectively, hygrometer sensors must, by their nature, be sensitive to changes in moisture content. It has been found, when measuring moisture content, that sensors which are initially "wet" take substantially longer to reach equilibrium than sensors which are initially in a "dry" state. The reason is that drying down a wet sensor to reach a measurement level takes longer than wetting up a dry sensor to the same level, due to the surface tension of the water on the wet sensor tending to resist the drying process.

Water vapour (a gas) is very mobile due to the Brownian motion of gases and quickly permeates spaces or pores in and around the sensor.

SUMMARY OF THE INVENTION

Accordingly, the invention provides a hygrometer for measuring the moisture content of a gas, comprising a chamber housing a hygrometer sensor, and a gas inlet for admitting gas into the chamber, a gas outlet for allowing gas to leave the chamber, the apparatus being such that a drying medium can be stored in the chamber to dry the sensor and then be rapidly removed from the chamber prior to measurement.

The gas may be air.

Preferably, the drying medium may comprise a dessicant package.

Preferably, the chamber has a removable lid.

The dessicant package may be inserted into the chamber by removing the lid and placing the package within the chamber.

Preferably, caps may be provided for blocking the gas inlet and gas outlet when the hygrometer is not in use.

The invention includes a method or measuring moisture content using the hygrometer.

Other objects and advantages will become apparent from the following description of embodiments of the invention, given by way of example.

PREFERRED EMBODIMENTS OF THE INVENTION

Figure 1:
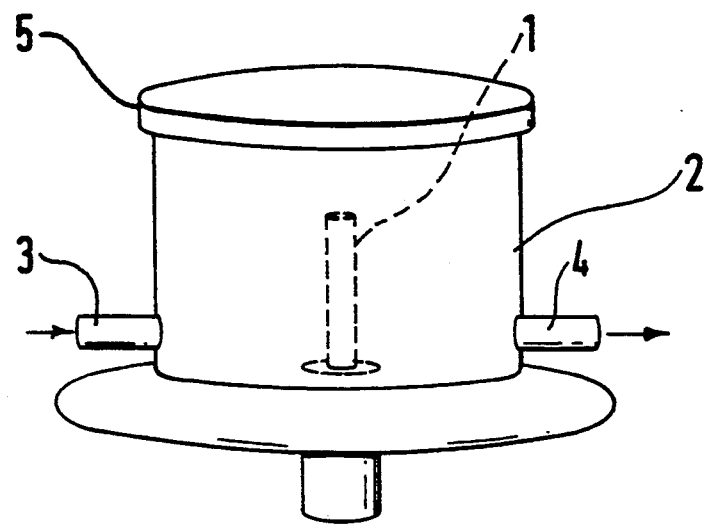
FIG. 1 shows a first embodiment of a hygrometer, according to the invention.

A first embodiment of a hygrometer is shown in FIG. 1. The hygrometer comprises a hygrometer sensor 1 housed within a chamber 2. The chamber has an air inlet 3, for admitting air into the chamber, and an air outlet 4 for allowing the air to escape. The chamber is provided with a removable lid 5, for allowing the insertion, or removal, of a dessicant package (not shown).

The provision of a removable dessicant package allows the hygrometer to be stored in a "dry" state rather than a "wet" state. The wet state would normally correspond to a room humidity of, say, 30,000 parts of moisture per million parts of air. A typical measurement level that a hygrometer might be called upon to monitor might be in the order of 100 parts per million.

Typically during storage, the air inlets and outlets 3 and 4 would be blocked by bungs or similar. When it is decided to make a measurement with the hygrometer, the air tight lid 5 may be removed, and the dessicant package extracted, before replacing the lid, removing the bungs from the inlet and outlet, attaching inlet and outlet tubes, if required, and operating the hygrometer.

Alternatively, the inlet and outlet bungs can be removed, whilst the dessicant package remains in place, allowing the hygrometer sensor to come to equilibrium with the air or gas being monitored for moisture content prior to removal of the dessicant.

Figure 2:
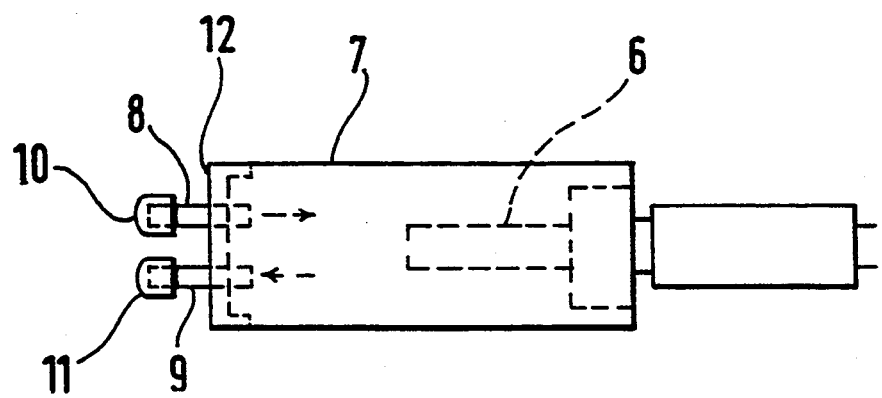
FIG. 2 shows a second embodiment of a hygrometer, according to the invention.

FIG. 2 shows a second embodiment of the invention, in which the hygrometer comprises a sensor 6, housed within a chamber 7. One end of the chamber 7 is attached to inlet and outlet ports 8 and 9, which have removable caps 10 and 11 respectively, mounted on a removable lid 12.

The embodiment of FIG. 2 operates in substantially the same manner as the embodiment of FIG. 1. The caps 10 and 11 are removable so that in use, tubes (not shown) may be attached to the inlet and outlet ports and air flowed past the sensor 6. The lid 12 may be unscrewed from the chamber for the insertion/removal of a dessicant.

Naturally, other methods of introducing a dessicant into a hygrometer chamber may be envisaged, for instance, a screw attachment may be provided on the chamber 2 or 7, for the connection of a cartridge and, when the dessicant is not required, the screw connection may be blanked off.

Whilst the invention has been described in relation to the monitoring of the moisture content in air, it will be appreciated that it may be used in conjunction with other gas monitoring equipment where there is a requirement for initial "dry" conditions.

The reader's attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such textures and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, Bach feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

I claim:

1. A hygrometer for measuring the moisture content of a gas comprising:
   a chamber;
   a hygrometer sensor housed within the chamber;
   a first opening comprising a gas inlet for admitting gas into the chamber during use;

a second opening comprising a gas outlet for allowing gas to leave the chamber during use;

third opening means, larger in size than said first and second openings, for inserting a drying medium into the chamber for storage in the chamber to dry the sensor prior to use, and for rapidly removing the drying medium when the hygrometer sensor is to be used;

closure means for closing the third opening while the drying medium is being stored in the chamber and while the hygrometer sensor is in use.

2. A hygrometer as claimed in claim 1, in which tile gas is air.

3. A hygrometer as claimed in claim 1, in which the drying medium comprises a dessicant package.

4. A hygrometer as claimed in claim 1, in which the chamber has a removable lid fitted over the third opening.

5. A hygrometer as claimed in claim 4, in which tile drying medium comprises a dessicant package, and the dessicant package is inserted into the chamber by removing the lid and placing the package within the chamber.

6. A hygrometer as claimed in claim 1, in which caps are provided for blocking the gas inlet and gas outlet for first and second openings when the hygrometer apparatus is not in use.

7. A method of measuring moisture content of a gas, using a hygrometer as claimed in claim 1.

8. A method of measuring moisture content of a gas comprising the steps of:

drying a hygrometer sensor mounted in a chamber by placing a drying medium into the chamber having first and second openings;

then removing said drying medium from the chamber;

then exposing said hygrometer sensor in the chamber to moisture containing gas; and then measuring a moisture content of said moisture containing gas.

9. A method of measuring moisture content on a gas as claimed in claim 8, further comprising:

flowing said moisture containing gas past said exposed hygrometer sensor from said first opening to said second opening.

* * * * *